(12) United States Patent
Feiweier et al.

(10) Patent No.: US 10,527,697 B2
(45) Date of Patent: Jan. 7, 2020

(54) METHOD AND IMAGING APPARATUS FOR OPTIMIZING A SIGNAL-TO-NOISE RATIO OF A MAGNETIC RESONANCE IMAGE

(71) Applicant: Siemens Healthcare GmbH, Erlangen (DE)

(72) Inventors: Thorsten Feiweier, Poxdorf (DE); Uvo Hoelscher, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/027,885

(22) Filed: Jul. 5, 2018

(65) Prior Publication Data
US 2019/0011520 A1 Jan. 10, 2019

(30) Foreign Application Priority Data
Jul. 5, 2017 (EP) .................................... 17179796

(51) Int. Cl.
*G01R 33/565* (2006.01)
*G01R 33/56* (2006.01)
*G01R 33/54* (2006.01)
*A61B 5/055* (2006.01)
*G01R 33/385* (2006.01)
*G01R 33/48* (2006.01)

(52) U.S. Cl.
CPC .......... *G01R 33/56* (2013.01); *G01R 33/543* (2013.01); *A61B 5/055* (2013.01); *G01R 33/3854* (2013.01); *G01R 33/4806* (2013.01)

(58) Field of Classification Search
CPC ................ G01R 33/246; G01R 33/50; G01R 33/56366; G01R 33/5659; G01R 33/583; G01R 33/4835; A61K 49/06
See application file for complete search history.

(56) References Cited

U.S. PATENT DOCUMENTS

| 5,416,412 | A | 5/1995 | Slayman et al. | |
|---|---|---|---|---|
| 7,479,783 | B2* | 1/2009 | Alsop | G01R 33/5615 324/307 |
| 8,076,939 | B2* | 12/2011 | Setsompop | G01R 33/246 324/309 |

(Continued)

OTHER PUBLICATIONS

Bartels, et al. "Improved Lumen Visualization in Metallic Vascular Implants by Reducing RF Artifacts", Magnetic Resonance in Medicine, vol. 47, pp. 171-180 (Year: 2002).*

(Continued)

*Primary Examiner* — Alesa Allgood
(74) *Attorney, Agent, or Firm* — Schiff Hardin LLP

(57) ABSTRACT

In a method and apparatus for optimizing the signal-to-noise ratio (SNR) of a magnetic resonance (MR) dataset acquired by means of a magnetic resonance system having at least one transmit coil, a measurement protocol for an acquisition that is to be performed in order to obtain the MR dataset of a predefined measurement volume. A deviation of an actual flip angle from the predefined flip angle in a specific area of the predefined measurement volume is determined for a preset transmitter scaling. The transmitter scaling of the RF pulse is adjusted in order to correct the actual flip angle so that the actual flip angle is approximated to the predefined flip angle in the specific area. The MR dataset is acquired with the adjusted transmitter scaling.

16 Claims, 3 Drawing Sheets

(56) References Cited

U.S. PATENT DOCUMENTS

| | | | |
|---|---|---|---|
| 9,594,145 B2* | 3/2017 | Lee | G01R 33/246 |
| 2005/0083054 A1 | 4/2005 | Feiweier et al. | |
| 2008/0111547 A1* | 5/2008 | Alsop | G01R 33/5615 |
| | | | 324/309 |
| 2010/0066361 A1* | 3/2010 | Setsompop | G01R 33/246 |
| | | | 324/309 |
| 2017/0089996 A1 | 3/2017 | Feiweier | |

OTHER PUBLICATIONS

Dardzinski, et al. "Spatial Variation of T2 in Human Articular Cartilage" Radiology, Radiological Society of North America, vol. 205, No. 2, 1997, pp. 546-550; (1997).

Bartels, et al. "Improved Lumen Visualization in Metallic Vascular Implants by Reducing RF Artifacts",magnetic Resonance in Medicine., vol 47, pp. 171-180, (2002).

\* cited by examiner

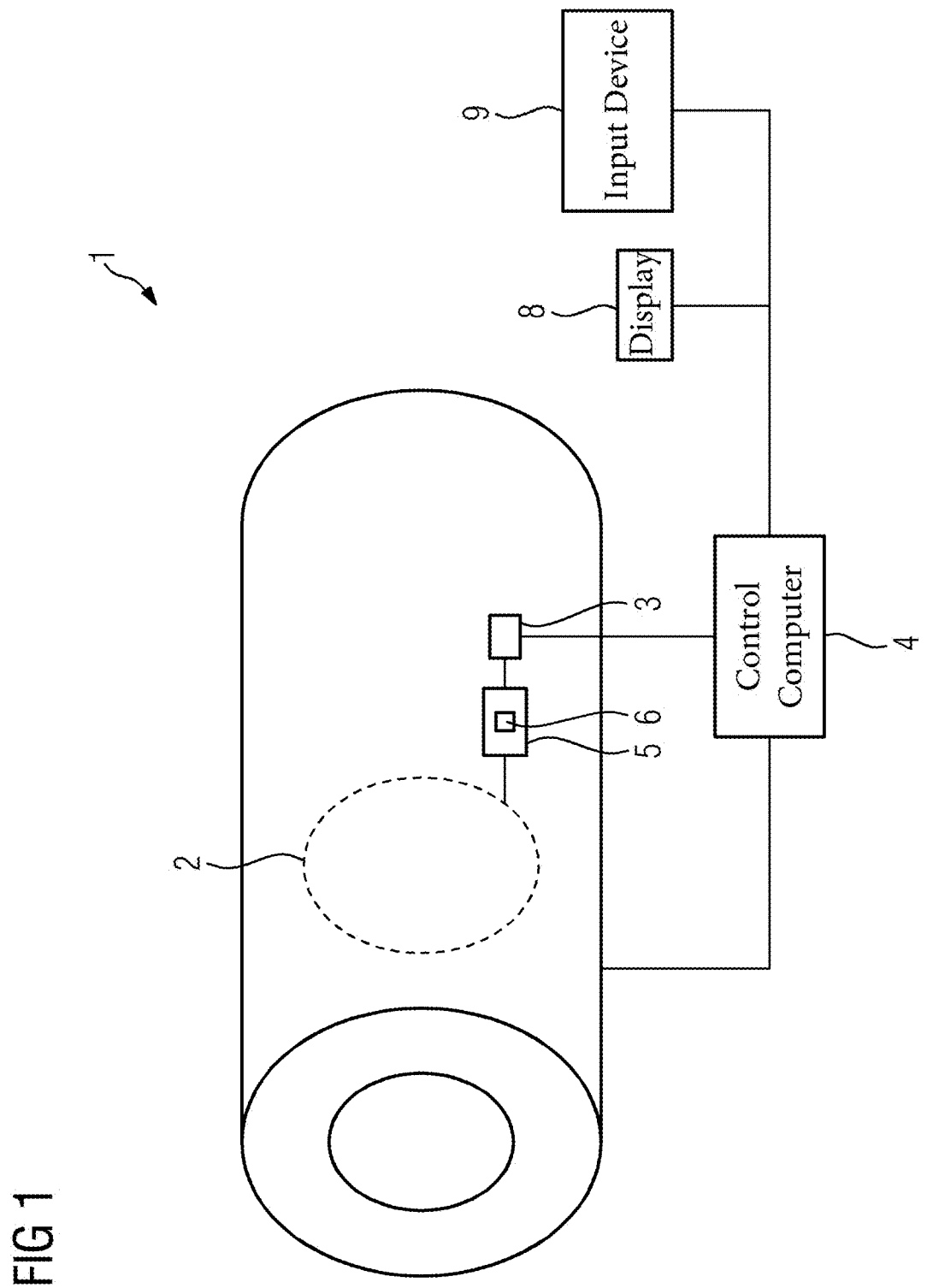

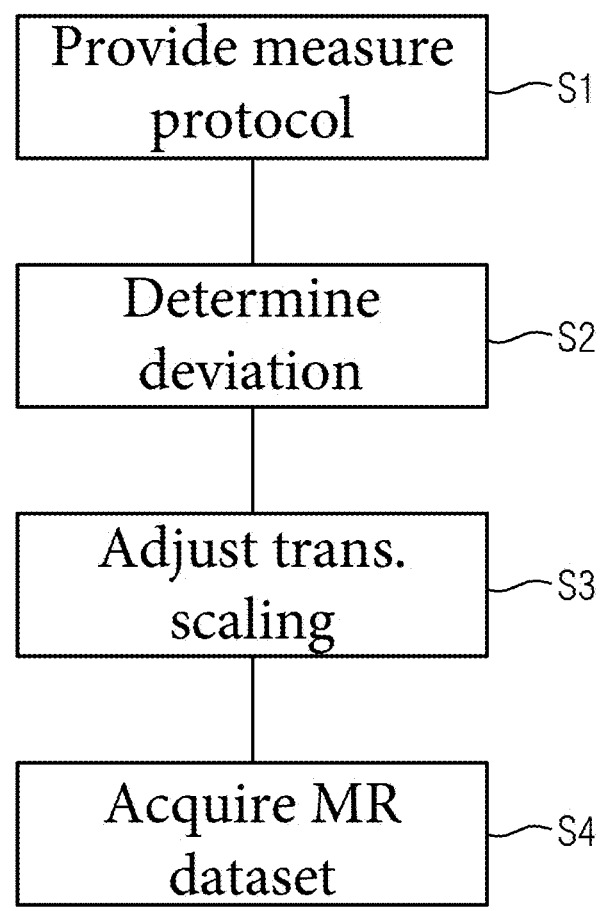

METHOD AND IMAGING APPARATUS FOR OPTIMIZING A SIGNAL-TO-NOISE RATIO OF A MAGNETIC RESONANCE IMAGE

BACKGROUND OF THE INVENTION

Field of the Invention

In the course of a magnetic resonance (MR) examination, a patient is positioned on a patient table, the local radio-frequency (RF) coil that is preferred for the examination, e.g. a knee coil or a head coil, is connected to the magnetic resonance scanner. Thereafter the patient is advanced into the tunnel of the magnetic resonance scanner. Adjustment measurements are thereupon carried out, inter alia, in order to accurately determine the resonance frequency and in order to fine-tune the shim coils that are used to compensate inhomogeneities in the basic magnetic field.

Once all preparatory activities have been completed, the actual diagnostic measurements can be performed. Measurement protocols are employed for this purpose. A measurement or scan protocol is a measurement sequence composed of preset parameters, the preset values being adjusted for specific examinations. The local RF coil, or another RF coil such as a whole body coil, radiates RF excitation or RF refocusing pulses into the patient, which give certain nuclear spins in the patient a magnetization that causes those excited nuclear spins to deviate from the field lines of a basic magnetic field by an amount known as a flip angle. As the excited nuclear spins relax and return to the steady state, they emit radio-frequency signals, called MR signals.

Description of the Prior Art

With typical measurement times in the range of a few minutes, the data acquisition for MR imaging is a relatively slow, albeit highly effective diagnostic tool. The duration of the measurement time is ultimately determined by the desired diagnostic quality of the MR images. One objective in MR imaging is to achieve a desired contrast in the MR images at the required resolution and with a sufficiently high signal-to-noise ratio (SNR).

A crucial factor in order to achieve this objective is for the SNR to reach at least a minimum value over the entire signal (data) acquisition area that is relevant to the diagnosis. The minimum value of the SNR is not necessarily of equal magnitude for all regions in the acquisition area. Rather, the SNR should be high in a region of interest, i.e. a critical area, whereas it may be lower in adjoining regions. The length of time required to acquire the MR images is consequently determined based on insuring that the necessary minimum SNR is reached in every relevant acquisition area. This can be accomplished, for example, by performing additional averaging operations. At the same time this leads to the condition of the minimum SNR being "overfulfilled" in the adjoining regions.

A specific example of this scenario is diffusion-weighted imaging in the head. For clinical magnetic resonance systems having magnetic field strengths of up to 3 T, reception coil configurations currently in use deliver a significantly lower SNR in the brain stem than in the periphery of the brain. However, a high-quality visualization of the brain stem, i.e. the acquisition of images of the brain stem at a high SNR, may be significant for certain diagnostic issues, while the regions adjoining the brain stem are of less significance for that diagnosis, and could therefore be scanned at a lower SNR.

Increasing the SNR is possible by a number of methods. For example, the SNR can be increased by repetition of the image acquisition, i.e. by signal averaging. This does, however, result in a longer measurement time. Furthermore, the repetition time TR, i.e. the time that elapses between two succeeding excitations of the same slice of a region, could be extended in order to increase the available longitudinal magnetization for each signal excitation. This also leads to a lengthening of the measurement time and, in addition, to changes in contrast. It is also conceivable to increase the basic magnetic field that is applied, though this results in higher costs for operating the magnetic resonance system. Increasing the size of the voxels, i.e. opting for a lower resolution in favor of thicker measured slices, leads to images that are less sharp and to partial volume effects.

In an acquisition of MR images or of an MR dataset during a magnetic resonance measurement, the problem thus exists if the SNR is increased overall of the regions from which MR data are acquired, that the measurement time is extended and, as a result, data from some regions are acquired with an overfulfilled SNR.

SUMMARY OF THE INVENTION

An object of the present invention is to provide a method for operating a magnetic resonance apparatus that achieves an increased SNR in regions of interest, without any of the above-cited disadvantages, in particular without an extension of the measurement time or a loss of resolution.

The object is achieved in accordance with the invention by optimizing the transmitter scaling of the RF transmitted (amplifier circuit) that feeds the RF coil that emits the excitation pulses, the transmitter scaling being optimized in at least one region of interest, before the actual MR measurement is performed, so that a criterion for a signal-to-noise ratio (SNR) is satisfied in the at least one region of interest. A criterion for a signal-to-noise ratio (SNR) includes, for example that the SNR is increased in an area of a local minimum without the SNR dropping below that increased value in other areas. The method for optimizing the signal-to-noise ratio (SNR) of a magnetic resonance (MR) dataset which is acquired by operation of a magnetic resonance scanner having at least one RE transmit coil, has the following steps.

A measurement protocol is provided to a computer, for an acquisition that is to be performed in order to obtain RE signals that form a magnetic resonance (MR) dataset from a predefined measurement volume, wherein the measurement protocol has at least one RF pulse, which is radiated by the at least one RF transmit coil with a predefined flip angle that is relevant to the signal amplitude of the RF signals. The computer determines a deviation of an actual flip angle from the predefined flip angle in a specific area of the predefined measurement volume for a preset transmitter scaling. The computer adjusts the transmitter scaling of the RF pulse in order to correct the actual flip angle, so that the actual flip angle is approximated to the predefined flip angle in the specific area. The computer then generates control signals, corresponding to the measurement protocol with the adjusted transmitter setting, and, with these control signals operates the MR apparatus (i.e., the MR data acquisition scanner thereof) in order to acquire the RF signals that form the MR dataset.

In a known manner, image data are reconstructed in the computer, or in another computer, or in another computer, from the acquired MR dataset, and the image data are provided to a display at which an MR image of the region of interest is then visually presented at a screen of the display.

According to the inventive method, a number of regions of interest can be specified in which the actual flip angle is determined and adjusted. Furthermore, the transmit coil may also serve as a reception coil, or the MR apparatus may have a separate reception coil and the reception sensitivity of the reception coil is determined in the region or regions of interest. Following an evaluation of the deviation of the predefined flip angle from the actual flip angle and of the reception sensitivity in a region of interest, the transmitter scaling is optimized such that an SNR criterion is fulfilled in the region of interest. Determining the deviation of the predefined flip angle from the actual flip angle is equivalent to estimating the effect of the flip angle on the SNR for a predefined measurement protocol. The SNR is consequently determined by the flip angle, by the reception sensitivity and by the measurement protocol.

The measurement volume may be a slice, a number of slices, or a volume (slab) of a 3D measurement. The specific area is preferably an area within a slice or volume, but may also be one of a number of slices.

As used herein, "transmitter scaling" means a setting of the flip angle by an appropriate actuation of the RF transmit coil, by which the signal amplitude or signal level of the RF pulses that are relevant to the MR measurement is driven or, as the case may be, increased or reduced depending on whether the flip angle is to be increased or reduced. The transmitter scaling is relevant with regard to the deflection of a longitudinal magnetization that is present. The transmitter scaling is typically set automatically by the control computer of the magnetic resonance apparatus such that the predefined flip angle is attained on average over a measurement volume. According to the invention, the transmitter scaling is adjusted in the measurement volume of interest such that a predefined SNR is achieved primarily in the region of interest, such as the brain stem, for example.

In order to determine the deviation of the actual flip angle from the predefined flip angle in a specific area of the predefined measurement volume for a preset transmitter scaling, measurement methods are used in which an actual spatial distribution of the attained flip angles for a preset transmitter scaling is measured directly. A spatially resolved flip angle map acquired in this way directly yields a deviation of the actual flip angle from the predefined flip angle. Such a measurement method is described in DE 103 38 074 B4, for example. The MR signal amplitude S(x) received at location x, and thus, as a consequence, the SNR, scales with the spatial sensitivity profile R(x) of the reception coil and the field profile of the transmit coil in the object T(x), i.e. the patient to be examined, according to $$S(x) \sim R(x) * f(\alpha(x)),$$

where $\alpha(x)$ is the local actual flip angle and is given by $$\alpha(x) = \gamma \int T(x) B_1(t) dt.$$

The constant $\gamma$ is the gyromagnetic ratio and $B_1(t)$ is the time curve of the RF pulse. The function $f(\alpha(x))$ specifies how, for a specific measurement method or a specific measurement protocol, the flip angle $\alpha(x)$ is translated into a signal-generating transverse magnetization of the nuclear spins. Thus, for a gradient echo experiment where TR>>$T_1$, for example, it is found that $f_{SE}(\alpha) \sim \sin(\alpha)$ applies, and, for a spin echo experiment ($\alpha$-2$\alpha$-Echo) where TR>>$T_1$, that $f_{SE}(\alpha) \sim \sin^3(\alpha)$ applies, and, for a double spin-echo experiment ($\alpha$-2$\alpha$-2$\alpha$-Echo) correspondingly, that $f_{SE}(\alpha) \sim \sin^5(\alpha)$ applies. Furthermore, more complex dependencies are known as the steady state of the magnetization, in the case of a shorter repetition time TR. The sensitivity profile R(x) of reception coils, in particular of multichannel variants and at a field strength of at least 3 T, is significantly lower in the center of the head (x=0) than in the periphery, i.e. at the edge, at (x=R). This is a reason why the SNR in conventional MR measurements is lower in the brain stem than in the periphery. Adjusting the actual flip angle to match the predefined flip angle in the regions of interest according to the inventive method consequently has the advantage that the acquisition of the MR dataset can be carried out with a homogenized SNR. As a result, a minimum measure for the SNR is attained in the regions of interest, and consequently an improved visualization of the regions of interest is possible, such that the resulting MR image demonstrates a higher diagnostic value, in particular better contrasts. The patient's exposure to RF radiation turns out to be higher or lower, depending on whether the adjusted transmitter scaling increases or reduces the flip angle or flip angles. In particular during 3T head imaging, there is generally a decrease in the patient's exposure to RF radiation, a positive effect of which is that faster acquisitions of the MR measurement data are possible, due to a reduction in the repetition time TR.

Preferably, the specific area is located in a region of minimum sensitivity of the reception coil, in particular in the area of the lowest sensitivity of the reception coil. Optimization in this region therefore causes the signal to be increased in this area; in other areas, in contrast, the flip angle has been made worse due to the transmitter scaling, as a result of which the signal decreases. Distributing the sensitivity of the reception coil results in an at least partial compensation for this effect during the reception of the signal: The high signal from the specific area is received at the lowest sensitivity. The signal-to-noise ratio is homogenized over the entire measurement volume as a result.

In an embodiment, the deviation of the actual flip angle from the predefined flip angle is determined by a measurement, either implemented by the control computer, or the results of which are provided to the control computer. In order to determine the deviation of the actual flip angle from the predefined flip angle in a specific area of the predefined measurement volume for a preset transmitter scaling, measurement methods can be used in which an actual spatial distribution of the attained flip angles for a preset transmitter scaling is measured directly. A flip angle map acquired in this way, in particular one that is spatially resolved, directly yields a deviation of the actual flip angle from the predefined flip angle. Such a measurement method is described in DE 103 38 074 B4, for example. The determination of the deviation influences the adjustment of the transmitter scaling.

In another embodiment, the deviation of the actual flip angle from the predefined flip angle is determined on the basis of empirical values that are stored in a database for the acquisition of magnetic resonance (MR) datasets of a specific body region in combination with a specific transmit coil. For this purpose, the acquired signals, which have been acquired for a specific transmit coil in the case of an applied RF pulse having a specific transmit level or a specific transmitter scaling, and, where appropriate, using a specific reception coil, are correlated with the parameters of the transmit coil and the applied magnetic field. During the correlation of these values, the deviation is determined by known optimization methods which, for example, employ a downhill simplex or a Levenberg-Marquardt algorithm or the like. With these methods, a cost function is determined and then a minimization of the cost function is carried out.

The transmitter scaling of the RF pulse is preferably adjusted such that the signal-to-noise ratio (SNR) lies above a minimum value in the entire predefined measurement volume. By adjustment of the transmitter scaling of the RF pulse such that the signal-to-noise ratio (SNR) lies above a minimum value in the entire predefined measurement volume, the signal-to-noise ratio (SNR) is homogenized over the entire measurement volume as a result of a minimum SNR being reached, thereby enabling a diagnostically valuable measurement signal to be acquired over the entire measurement volume.

In order to homogenize the signal-to-noise ratio over the predefined measurement volume, the signal-to-noise ratio is preferably reduced in areas of the region of the object that is to be examined that have a high SNR, in particular in areas of the periphery, and/or increased in areas of the region of the object that is to be examined that have a low SNR, in particular in a central area. The SNR is consequently homogenized across the region of the object that is to be examined.

In order to adjust the transmitter scaling, empirical values are preferably used that are stored in a database for the acquisition of a magnetic resonance (MR) dataset of a specific body region in combination with a specific reception coil. Preferably, the empirical values for a specific body region are stored in combination with a specific reception coil and/or a specific transmit coil for a predefined magnetic field.

Also preferably, the transmitter scaling is adjusted on the basis of at least one of the following items of information:
  a sensitivity profile of the reception coil that is known or is determined by measurement,
  a spatial distribution of the deviation of the actual from the predefined flip angle in the predefined measurement volume,
  the dependence of the relative signal level on the flip angle.

The sensitivity profile of the reception coil may be stored in a database or may be acquired before an MR diagnostic is performed. When a spatial distribution of the deviation of the actual from the predefined flip angle in the predefined measurement volume is used, it is possible to make use of empirical values stored in a database. It is also conceivable to measure the spatial distribution at the present time and to use the same for the pending MR measurement. To that end, a deviation of the actual flip angle is measured in a spatially resolved manner in different slices, in particular in the entire region of which images are to be acquired. It is furthermore possible to evaluate the dependence of the relative signal level on the flip angle, or to obtain such empirical values from a database. For this purpose, the actual flip angle is correlated with the associated signal level. It is also possible to use one or more of the items of information for the purpose of adjusting the transmitter scaling. The adjustment of the transmitter scaling overall is optimized as a result.

Preferably, all of the cited items of information is available and the transmitter scaling is determined by an optimization method such that the expected relative signal level does not fall below a predefined minimum value at any location in the predefined measurement volume. Preferred optimization methods are methods for optimizing nonlinear functions such as the downhill simplex method or the Levenberg-Marquardt method. The predefined minimum value corresponds to a minimum SNR that is determined by the flip angle, by the reception sensitivity and/or by the measurement protocol. In particular, the minimum value of the SNR is around at least 5, preferably around 10, and particularly preferably around 20.

The method is preferably applied to all RF pulses of a measurement protocol that are relevant to the signal amplitude, i.e. excitation and refocusing pulses. In order to achieve a predetermined contrast or a suppression of specific signal contributions, additional pulses are preferably used for which no transmitter scaling is performed; in particular, an inversion pulse (IR) and/or a chemically selective saturation pulse (CSat) and/or a spatially selective suppression pulse (RSat) are/is used.

Preferably, the predefined measurement volume is composed of a number of slices and the transmitter scaling is performed independently for each slice. The method according to the invention may be combined with techniques in which the transmitter scaling can be adjusted individually for each slice ("dynamic adjustments" or "slice adjust"). At the same time the above-described optimizations of the transmitter scaling are carried out for each subvolume (single slice or single slab).

Preferably, the predefined measurement protocol provides a slice multiplexing method. With this, sub-pulses of a simultaneous excitation and the sub-volumes acquired during a refocusing are captured and analyzed individually. Each sub-pulse can then be optimized or scaled independently, for example. It is furthermore possible to combine the inventive method with other techniques in which the transmitter scaling can be adjusted individually for each slice. In this case the optimizations of the transmitter scaling are performed for each sub-volume or for each slice.

In a further embodiment, the specific area is selected automatically. The specific area may be stored in a measurement protocol which has been selected for performing the examination by MR imaging. It is equally conceivable to determine the specific area for an impending examination manually, if necessary, or to increase or reduce the size of the same manually. It is furthermore possible to define a number of specific areas. An increased SNR is thereby achieved, particularly in regions of great interest, while a lower SNR is achieved in the respective adjoining regions.

Preferably, the specific area may be selected by a user. Different predefined, predetermined areas may be stored in a selected measurement protocol. It is furthermore possible for the selected specific area to be increased or reduced in size manually by the user if necessary for an impending examination.

The present invention also encompasses a magnetic resonance apparatus having at least one control computer that is configured to perform one of the above-described methods.

Preferably, the magnetic resonance apparatus has an input device that displays selection options for choosing the specific region of an object to a user, in particular the selection option "optimize brain stem", or graphical selection options. In the case of a graphical selection option, for example, an examination object, such as a human being can be displayed schematically on a screen, with different regions being proposed visually for the examination. This has the advantage that a user can quickly select a predefined measurement protocol without any need for the user to be particularly familiar with the magnetic resonance apparatus.

Further advantageous embodiments of the method according to the invention as discussed above correspond to equivalent embodiments of the magnetic resonance apparatus according to the invention.

The present invention also encompasses a non-transitory, computer-readable data storage medium encoded with programming instructions (program code) that, when the storage medium is loaded into a computer or computer system of an MR apparatus, cause the computer or computer system to operate the MR apparatus so as to implement any or all embodiments of the method according to the invention, as described above.

The inventive method, magnetic resonance apparatus, and electronically readable data medium are not limited to imaging of the head. Rather, they are applicable in all situations in which the signal amplitude can be increased by a locally optimized, adjusted flip angle at the location of the minimum reception coil sensitivity.

BRIEF DESCRIPTION OF THE DRAWINGS

FIG. 1 schematically illustrates a magnetic resonance apparatus.

FIG. 2 is a flowchart of the inventive method.

DESCRIPTION OF THE PREFERRED EMBODIMENTS

Figure 4:
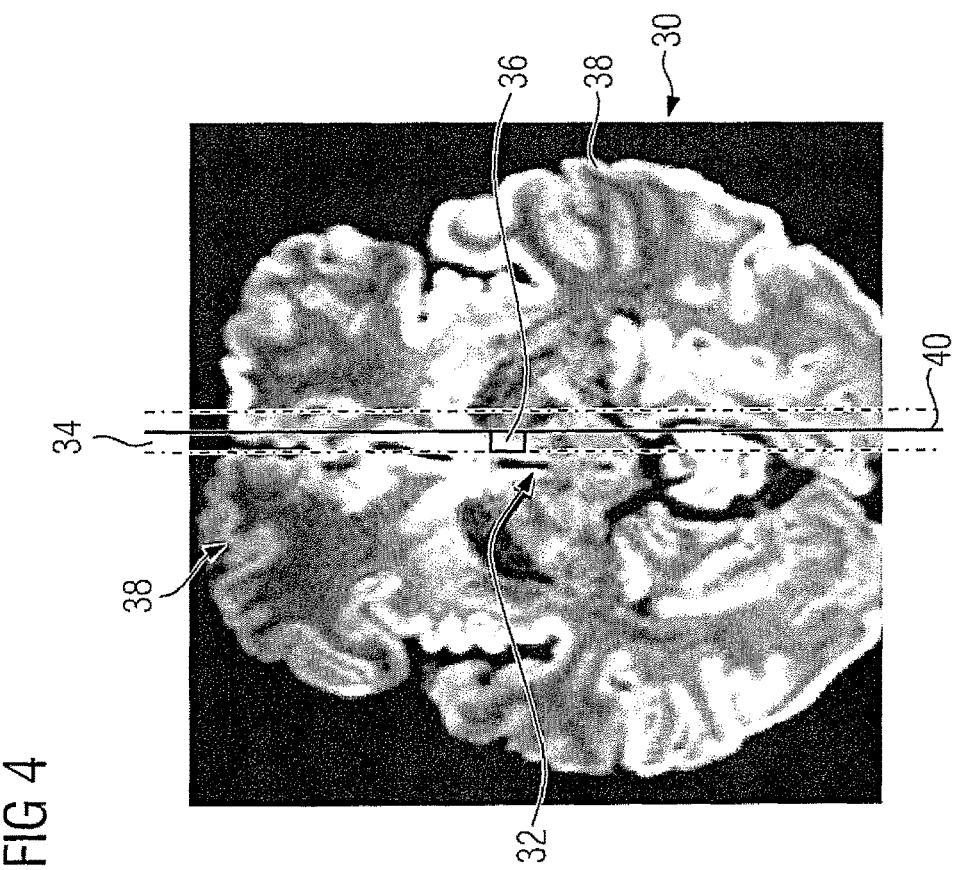
FIG. 4 shows an MR image of a head at the level of the brain stem, this image having been acquired using the inventive method.

FIG. 1 shows a magnetic resonance apparatus having a scanner 1 with at least one RF coil 2 that serves at least for transmission of RF signals, but that may also receive RF signals. The RF coil 2 is connected to the control computer 4 of the magnetic resonance apparatus via a terminal 3 that enables an electrical connection. The terminal 3 may be a plug-and-socket connection. The terminal 3 enables different RF coils 2 to be connected to the control computer 4. FIG. 1 is obviously a simplified representation, since there are generally more components than just the terminal 3 disposed between the RF coil 2 and the control computer 4 of the magnetic resonance apparatus.

The RF coil 2 has an information medium 5 that carries an information code 6 serving as a coil identification code. For example, the identification code 6 can be a numerical sequence, such as the digits 124, which e.g. stand for a specific head coil.

A display device 8 and an input device 9 are also connected to the control computer 4. Different specific areas 36 can be displayed graphically on a screen of the display device 8.

The described method is preferably implemented by the execution software, i.e. as a computer program, in the control computer 4. The computer program is in the form of electronically readable program codes stored on a data storage medium that is loaded into a memory of the control computer 4. The program code, when executed by the control computer 4, causes the control computer 4 to operate the magnetic resonance apparatus so as to implement the method as described below, and/or any of the embodiments described elsewhere herein. Although the control computer 4 is schematically represented in FIG. 1 as a single block, the control computer 4 may be composed of a number of computers or processors that are in communication with each other via hardwired connections or wireless communication links.

FIG. 2 is a flowchart of the inventive method for operating the magnetic resonance system 1 comprising the steps S1 to S4.

In the first step S1, a measurement protocol is provided for an acquisition that is to be performed in order to obtain a magnetic resonance (MR) dataset of a predefined measurement volume, wherein the measurement protocol comprises at least one RF pulse having a predefined flip angle $\alpha_{nominal}$ that is relevant to the signal amplitude S(x).

In the second step S2, a deviation of an actual flip angle $\alpha(x)$ from the predefined flip angle $\alpha_{nominal}$ in a specific area 36 of the predefined measurement volume, which according to FIG. 4 is slice 30, is determined for a preset transmitter scaling.

In the third step S3, the transmitter scaling of the RF pulse is adjusted in order to correct the actual flip angle $\alpha(x)$, such that the actual flip angle $\alpha(x)$ is approximated to the predefined flip angle $\alpha_{nominal}$ in the specific area. An optimized transmitter scaling in a slice 30 to be examined of the region may be determined empirically, for example. For this purpose, empirical values that are associated with a specific region of the body, such as the head or the knee, for example, may be stored in a database in combination with a specific reception coil 2, such as a 64-channel head coil, for example. The RF coil 2 may be embodied as a transmit coil 2 or as a coil acting as a transmit and reception coil.

Next, in the fourth step S4, the acquisition of a magnetic resonance (MR) dataset is performed using the adjusted transmitter scaling.

Figure 3:
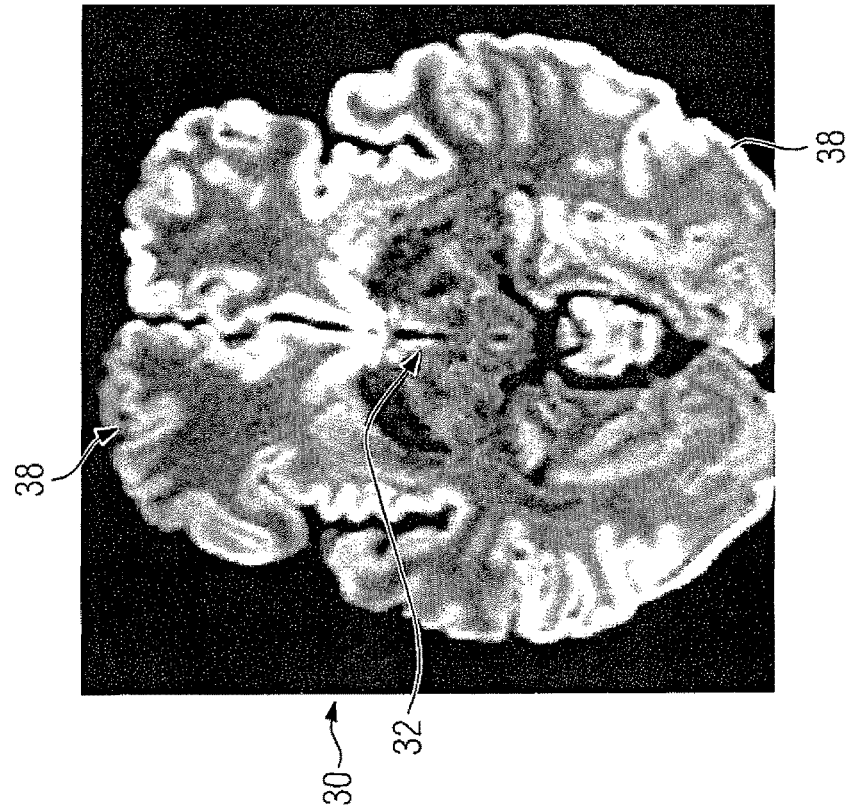
FIG. 3 shows an MR image of a head at the level of the brain stem, this image having been acquired using a conventional technique.

FIG. 3 shows a conventionally acquired MR image and, by way of comparison, FIG. 4 shows an image acquired by means of the inventive method, said image being an axial MR diffusion-weighted image of a slice 30 of the head of a patient at the level of the brain stem 32.

Both diffusion-weighted images of FIGS. 3 and 4 were acquired at a relatively high resolution with an applied magnetic field of 3 T and using a 64-channel head coil. When a magnetic field of 3 T is used, the predefined flip angle of, for example, $\alpha=90°$ for the excitation pulse is achieved over the entire head only as the spatial average in the case of conventional MR measurements. In the center of the head at x=0, the actual flip angles deviate in the case of conventional methods for example by 10% to 15% from the predefined flip angle. As a result, only a reduced SNR is achieved in the case of conventional methods.

FIG. 3 shows a conventionally acquired MR image in which the transmitter scaling is set by the system in such a way that the predefined flip angle $\alpha_{nominal}$ is achieved on average. The signal-to-noise ratio SNR is lower in the brain stem 32 than in the periphery 38, since the reception coil used has a low sensitivity R(x) in the area of the brain stem 32.

The method according to the invention is effective in particular when—as in the case of imaging of the head at 3 T using multichannel reception coils—the region of
   minimum reception coil sensitivity simultaneously has a
      suboptimal flip angle for the signal analysis:
   1. Determining the deviation of the actual local flip angle from the nominal value for this region.
   2. Adjusting the transmitter scaling of the RF pulses that are relevant to the signal amplitude in such a way that the nominal value is achieved locally.
   3. Performing the measurement.
   A homogenization of the SNR is achieved in this way:
   The SNR is increased in the region having the lowest reception coil sensitivity (in the brain stem, for example).
   The SNR is reduced if necessary in regions having higher reception coil sensitivity (in the periphery of the head, for example).

The nominal flip angle corresponds to an optimal SNR value in particular in the case of spin-echo measurements. In the case of other measurements, in contrast, the nominal flip angle does not necessarily exhibit a maximum SNR. Rather, the flip angle may also be set in such a way that an optimal contrast is achieved.

FIG. 4 shows an increased SNR in the area of the brain stem 32. During the acquisition according to FIG. 4, the transmitter scaling was adjusted such that the predefined flip angle was achieved in the center of the head, i.e. in the brain stem 32. As a result, the nominal value was achieved locally, in particular in a subregion 34 of the slice 30. As shown, the subregion 34 includes the specific area 36. The reference numeral 40 designates a centerline along the subregion 34. As a result hereof, the SNR has therefore been significantly increased in the area of the brain stem 32. At the same time, an adequate SNR, preferably the minimum SNR, has been preserved in the periphery 38 even though the flip angle α has diverged even further from the predefined flip angle in the area of the periphery 38 as a result of the transmitter scaling. The sufficiently high SNR is attributable to the high reception coil sensitivity in that area.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for optimizing a signal-to-noise ratio (SNR) of a magnetic resonance (MR) dataset, said method comprising:
   providing a computer with a measurement protocol designed to operate an MR data acquisition scanner, comprising a radio-frequency (RF) transmitter circuit that includes at least one RF transmit coil, in order to acquire RF signals that form said MR dataset, including operating said transmitter circuit to radiate, via said at least one transmit coil, at least one RF pulse having a defined flip angle that gives said RF signals a signal amplitude;
   in said computer, determining a deviation of an actual flip angle that occurs in a specific area of a defined measurement volume of the subject from which the RE signals are acquired, from a defined flip angle in said specific area produced by a preset transmitter scaling of said at least one RF pulse in said measurement protocol;
   in said computer, adjusting the transmitter scaling of the at least one RF pulse in said measurement protocol in order to reduce said deviation so as to make said actual flip angle coincide with said defined flip angle as closely as possible, thereby revising the measurement protocol so as to include the adjusted transmitter scaling; and
   generating control signals in said computer corresponding to the revised measurement protocol, with the adjusted transmitter scaling, and providing the control signals to the MR data acquisition scanner and thereby operating the MR data acquisition scanner to acquire said MR dataset with said adjusted transmitter scaling.

2. A method as claimed in claim 1 wherein said MR data acquisition scanner comprises a reception coil with which said RF signals are received, and wherein said specific area is situated in a region of minimum reception sensitivity of said reception coil.

3. A method as claimed in claim 1 comprising determining said deviation by operating said MR data acquisition scanner with said measurement protocol, and detecting the actual flip angle in the subject that is produced by said measurement protocol.

4. A method as claimed in claim 1 comprising determining said deviation by accessing, from said computer, a database comprising empirical values that represent MR datasets of different body regions acquired with different RF transmit coils, and selecting one of said values for which the body region and the RF transmit coil correspond to the specific area of the defined measurement volume, and the RF transmit coil of the MR data acquisition scanner, most closely correspond.

5. A method as claimed in claim 1 comprising adjusting said transmitter scaling to cause the SNR to be above a minimum value over an entirety of said defined measurement volume.

6. A method as claimed in claim 1 comprising the transmitter scaling in order to homogenize the SNR over said defined measurement volume by selectively reducing said SNR in portions of said defined measurement volume that have a high SNR and reducing said SNR in portions of said measurement volume that have a low SNR.

7. A method as claimed in claim 6 wherein said portions of said defined measurement volume that have said high SNR are situated at a periphery of said measurement volume, and said portions of said defined measurement volume that have a low SNR are situated in a central part of said defined measurement volume.

8. A method as claimed in claim 1 wherein said MR data acquisition scanner comprises a reception coil, with which said RF signals are received, and comprising adjusting said transmitter scaling based on at least one of a sensitivity profile of said reception coil, a spatial distribution of said deviation in said defined measurement volume, and a relative signal level of said flip angle.

9. A method as claimed in claim 8 comprising adjusting said transmitter scaling using all of said information by executing an optimization algorithm in said computer that ensures that said relative signal level does not fall below a predetermined minimum value at any location in said defined measurement volume.

10. A method as claimed in claim 8 comprising using said transmit coil also as said reception coil.

11. A method as claimed in claim 1 wherein said defined measurement volume comprises a plurality of slices, and adjusting said transmitter scaling independently for each slice in said plurality of slices.

12. A method as claimed in claim 11 comprising operating said MR data acquisition scanner with said measurement protocol in order to acquire said MR dataset with slice multiplexing.

13. A method as claimed in claim 1 comprising selecting said specific area of said defined measurement volume automatically in said computer.

14. A method as claimed in claim 1 comprising selecting said specific area of the measurement volume by providing a manual input to said computer that designates said specific area.

15. A magnetic resonance (MR) apparatus comprising:
   an MR data acquisition scanner comprising a radio-frequency (RF) transmitter circuit that includes at least one RF transmit coil;
   a computer provided with a measurement protocol designed to operate said MR data acquisition scanner in order to acquire RF signals that form an MR dataset, including operating said transmitter circuit to radiate, via said at least one transmit coil, at least one RF pulse having a defined flip angle that gives said RF signals a signal amplitude;

said computer being configured to determine a deviation of an actual flip angle that occurs in a specific area of a defined measurement volume of the subject from which the RF signals are acquired, from a defined flip angle in said specific area produced by a preset transmitter scaling of said at least one RF pulse in said measurement protocol;

said computer being configured to adjust the transmitter scaling of the at least one RF pulse in said measurement protocol in order to reduce said deviation so as to make said actual flip angle coincide with said defined flip angle as closely as possible, thereby revising the measurement protocol so as to include the adjusted transmitter scaling; and said computer being configured to generate control signals corresponding to the revised measurement protocol, with the adjusted transmitter scaling, and to provide the control signals to the MR data acquisition scanner and thereby operate the MR data acquisition scanner to acquire said MR dataset with said adjusted transmitter scaling.

16. A non-transitory, computer-readable data storage medium encoded with programming instructions, said storage medium being loaded into a computer system of a magnetic resonance (MR) apparatus comprising an MR data acquisition scanner that has a radio-frequency (RF) transmitter circuit comprising at least one RF transmit coil, said programming instructions causing said computer system to:

receive a measurement protocol designed to operate said MR data acquisition scanner in order to acquire RF signals that form said MR dataset, including operating said transmitter circuit to radiate, via said at least one transmit coil, at least one RF pulse having a defined flip angle that gives said RF signals a signal amplitude;

determine a deviation of an actual flip angle that occurs in a specific area of a defined measurement volume of the subject from which the RE signals are acquired, from a defined flip angle in said specific area produced by a preset transmitter scaling of said at least one RF pulse in said measurement protocol;

adjust the transmitter scaling of the at least one RE pulse in said measurement protocol in order to reduce said deviation so as to make said actual flip angle coincide with said defined flip angle as closely as possible, thereby revising the measurement protocol so as to include the adjusted transmitter scaling; and generate control signals corresponding to the revised measurement protocol, with the adjusted transmitter scaling, and provide the control signals to the MR data acquisition scanner and thereby operate the MR data acquisition scanner to acquire said MR dataset with said adjusted transmitter scaling.

* * * * *